United States Patent [19]

Kolesar, Jr.

[11] Patent Number: 4,893,108
[45] Date of Patent: Jan. 9, 1990

[54] HALOGEN DETECTION WITH SOLID STATE SENSOR

[75] Inventor: Edward S. Kolesar, Jr., Beavercreek, Ohio

[73] Assignee: The United States of America as represented by the Secretary of the Air Force, Washington, D.C.

[21] Appl. No.: 211,006
[22] Filed: Jun. 24, 1988
[51] Int. Cl.⁴ .............................................. H01L 7/00
[52] U.S. Cl. ........................................ 338/34; 73/23; 422/88
[58] Field of Search ...................... 338/34, 35; 422/88, 422/89, 90, 91, 92; 73/23, 23.1, 29; 204/411, 412, 195 R, 1 T

[56] References Cited

U.S. PATENT DOCUMENTS

| Re. 31,915 | 6/1985 | Oswin et al. | 204/412 |
| 4,130,797 | 12/1978 | Hattori et al. | 324/65 P |
| 4,225,410 | 9/1980 | Pace | 204/195 R |
| 4,267,023 | 5/1981 | Frant et al. | 204/1 T |
| 4,423,407 | 12/1983 | Zuckerman | 338/34 |
| 4,456,902 | 6/1984 | Komine et al. | 338/34 |
| 4,472,356 | 9/1984 | Kolesar, Jr. | 422/88 |
| 4,492,614 | 1/1985 | Welsh | 204/1 T |
| 4,549,427 | 10/1985 | Kolesar, Jr. | 422/88 |
| 4,571,292 | 2/1986 | Lin et al. | 204/412 |
| 4,580,439 | 4/1986 | Manaka | 73/23 |
| 4,584,867 | 4/1986 | Forster | 73/23 |
| 4,627,269 | 12/1986 | Forster | 73/23 |
| 4,666,628 | 5/1987 | Uchikawa | 338/34 X |

OTHER PUBLICATIONS

"Elektrische Leitfahigkeit von Anionenaustauscher-membranen" by von G. Manecke und K. F. Bonhoeffer, Z. Electrochem, West Germany, vol. 55, No. 6, p. 475, Aug. 1951.

"Conductance and Water Transfer in a Leached Cation-Exchange Membrane" by J. G. B. George and R. A. Courant, Journal of Physical Chemistry, Jan. 57, pp. 246-249.

"Electrostatic Phenomena in Ion Exchange Membranes" by S. D'Alessandro and A. Tantillo, Elsevier Publishing Co., Amsterdam, Oct. 1969.

"Permeation Through a Membrane with Mixed Boundary Conditions: " by R. M. Barrer, J. A. Barrie and M. G. Rogers, Faraday Society, (British), vol. 58, No. 480, part 12, Dec. 1962, pp. 2473-2483.

Primary Examiner—Bruce A. Reynolds
Assistant Examiner—Marvin M. Lateef
Attorney, Agent, or Firm—Gerald B. Hollins; Donald J. Singer

[57] ABSTRACT

A solid state thin film detection and measurement apparatus for halogen gas components such as chlorine in a gas mixture is described. The detection cell employs plural response modes to the halogen gas including response to the thermal effect of a halogen and thin film reaction and response to the thermal and ion diffusion effects of the halogen reaction with a halide supporting substrate member. These plural responses are manifested by an electrical resistance change in the thin film element and this change is sensed with a four-lead measurement arrangement. The use of plural measurement cells each of a different composition and computerized multiplexing of thin film resistance signals is included as are identification of possible thin film and substrate compositions.

18 Claims, 3 Drawing Sheets

HALOGEN DETECTION WITH SOLID STATE SENSOR

RIGHTS OF THE GOVERNMENT

The invention described herein may be manufactured and used by or for the Government of the United States for all governmental purposes without the payment of any royalty.

BACKGROUND OF THE INVENTION

This invention relates to the field of halogen element presence sensing and concentration measurement using solid state electrically responsive sensing elements.

An increased current awareness of the dangers attending both prolonged and intense exposure to chemicals in the environment has increased the need for sensitive and easily used detection apparatus. This awareness coincides with the increased popularity of chlorine and other halogen inclusive compounds as cleaning agents, sterilizing agents, chemical reactants, chemical weapons—involving biological and vertabraed object defense, and other industrial reactants. These chlorine and halogen containing materials have been recognized as significant threats to human welfare and, therefore, are deserving of careful precaution in exposure avoidance. Notwithstanding the awareness of potential harm from exposure to these compounds and their constituents, a satisfactory arrangement for measuring worker exposure and determining concentrations of these agents in an atmosphere has been unduly limited by the complexity and cumbersome nature of the heretofore used halogen responsive measurement apparatus. Many currently available chlorine detectors, for example, use the phenomenon of gas adsorption followed by dissolution in an electrolyte which contains bromine ions. A subsequent chemical oxidation reaction with these bromine ions yields an electrical current which has a magnitude that is proportional to the reaction kinetics. A significant limitation of this detector concept, making it inconvenient to use, is the need for a liquid electrolyte in its operation. Periodic replenishment of this electrolyte is essential and, therefore, creates a significant logistics burden which attends use of such instrumentation. In addition to this use burden, it is not possible to make a precise determination of the concentration of chlorine gas in the atmosphere using this detector apparatus since its indication is of a yet or no nature. The integrated solid state detector element is particularly attractive as an improvement on this existing detector technology and is therefore employed in the present invention measuring apparatus.

SUMMARY OF THE INVENTION

The present invention provides for the detection of chlorine and other gaseous halogen compounds with a solid state detector cell. In the detector cell, the halogen reacts with two portions of the cell structure. In this double reaction, the heat generated electrical resistance change in a thin film element component of the detector cell is supplemented by the heat generation and other effects attending a second reaction. The second reaction occurs between the encountered halogen element and the substrate member which bears or supports the thin film element. The thermal effects of these two reactions is additionally supplemented by an ion exchange phenomenon between the resistance element and the substrate member that also contributes to the change of resistance in the thin film member. Additional aspects of the invention involve use of detector cell elements selected in accordance with a specific chemical and thermodynamic selection criteria and the use of plural detection cells, each of a different response character to the halogen element being detected, in an array capable of unique halogen element identifications. Another aspect of the invention involves the use of a precision electrical resistance measurement technique in the thin film sensing element and correlation of the resistance change with both an absolute and a relative reference criteria.

It is an object, therefore, of the present invention to provide a solid state halogen detection element which employs a dual reaction sensing mechanism.

It is another object of the invention to provide a detection cell in which a response to a sequence of exposure events is cumulative.

It is another object of the invention to provide a cumulative effect detection cell in which the results of an individual exposure event can be time segregated.

It is another object of the invention to provide a thermally operating detection cell in which a plurality of chemical and/or physical reaction phenomena contribute to a measurable electrical characteristic change.

It is another object of the invention to provide a detection cell wherein the contribution of two chemical and/or physical reactions to a sensed condition are coupled together using a plurality of coupling mechanisms.

It is another object of the invention to provide a detection cell in which thermal or heat energy coupling between detection cell sensing elements is supplemented by ionic transfer between sensing elements.

It is another object of the invention to provide a sensing cell which operates on the principal of the Gibbs free energy relationship in a chemical/physical reaction.

It is another object of the invention to provide a sensing cell which can be fabricated from a plurality of different metallic and metallic halide combination parts.

It is another object of the invention to provide a detection cell arrangement in which a plurality of detecting component cells, each of a different metal plus metal halide pairing composition, provide a multiple approach identification of the halogen element being detected.

Additional objects and features of the invention will be understood from the following description and the accompanying drawings.

These and other objects of the invention are achieved by an apparatus for detecting the presence of gaseous first halogen components in an unknown mixture of gases which includes the combination of a detection substrate member comprised of a second halogen chemical compound of a first metal; a thin film electrical resistance detector element received on said substrate member and comprised of a second metal in metallic form; an apparatus for moving a stream of said unknown gas mixture over said detection substrate and detector elements; an apparatus responsive to the combined detector element unknown gas exposure and the substrate member unknown gas exposure resistance changes in said detector element for indicating the presence of said first halogen components in said unknown mixture of gases.

DETAILED DESCRIPTION

Figure 1:
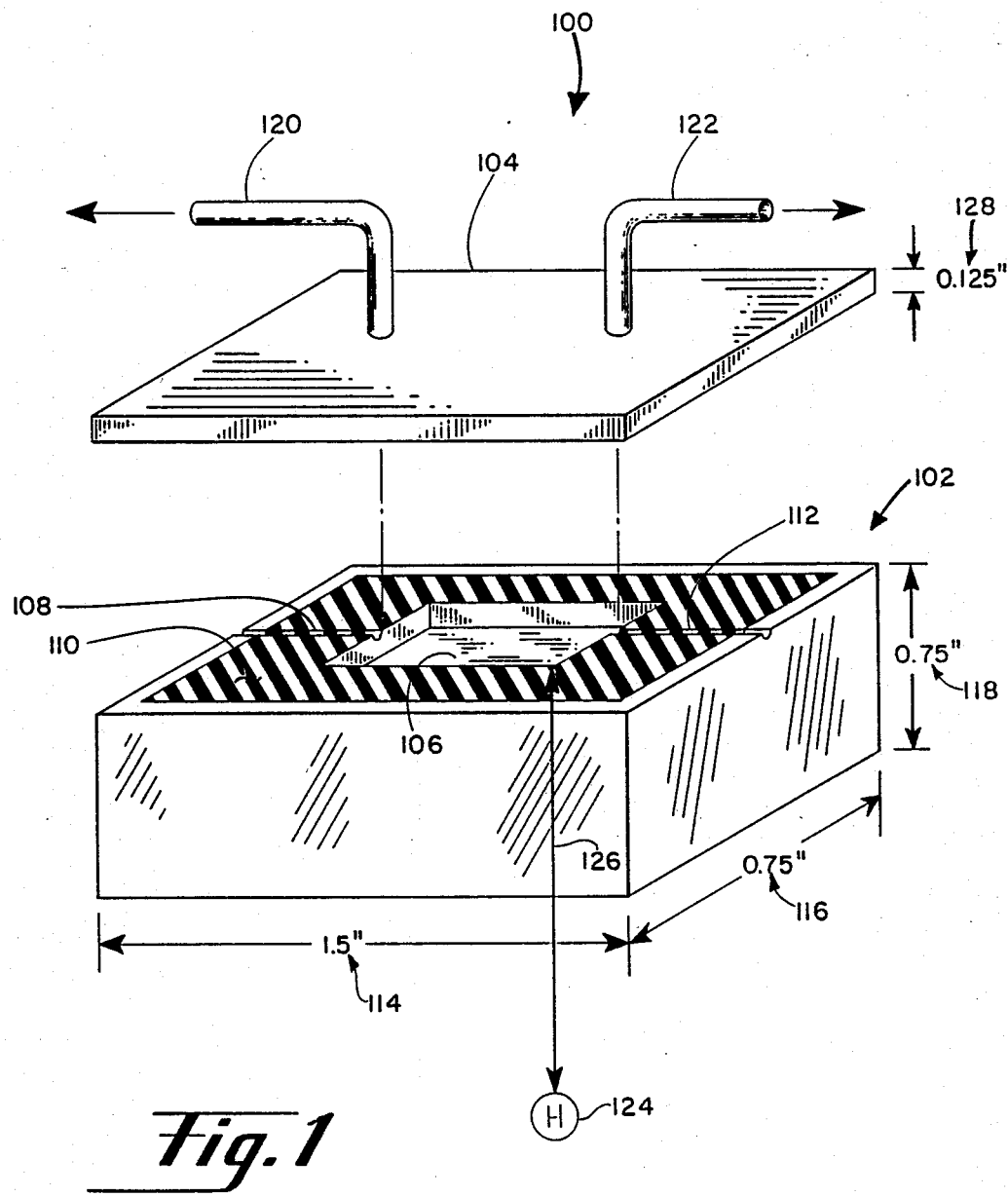
FIG. 1 shows the physical arrangement of a halogen detector apparatus.

FIG. 1 in the drawings shows an overall perspective exploded view of a halogen detector apparatus made in accordance with the invention. The detector apparatus 100 in FIG. 1 is comprised of a closable housing member 102 which is arranged to receive a closure member 104 in a gas impervious fitted relationship. The housing 102 and enclosure member 104 in FIG. 1 may be fabricated of plastic, polymeric, or possibly ceramic materials or other materials known in the art. The housing 102 may be fabricated as either an integral one-piece structure or as five individually fitted together pieces. The closure member 104 is held in a gas-tight fitted relationship with the housing 102 by way of machine screws or other fastening arrangements which are not shown in FIG. 1.

Figure 2:
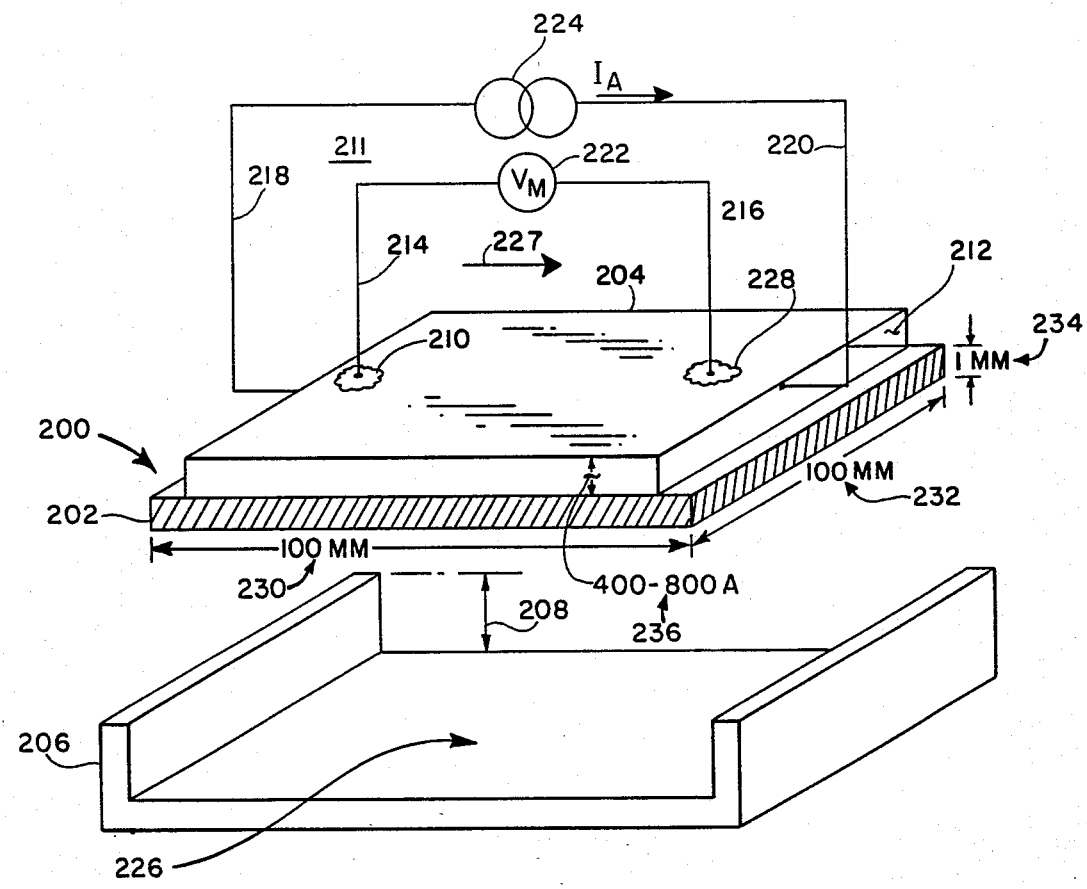
FIG. 2 shows the structure of a thin film detection cell usable in the FIG. 1 detector apparatus.

Received in the housing 102 in FIG. 1 is a cavity receptacle 106 that is capable of containing a halogen element detection cell of a type shown in FIG. 2 in the drawings. The receptacle 106 is surrounded by thermal insulating material 110 which fills the space between the receptacle and the interior walls of the housing member 102.

Communicating between the receptacle 106 and the exterior of the housing member 102 are a pair of pressure sealable conduit paths 108 and 112 by which electrical conductors described below may communicate with the detection cell apparatus received in the receptacle 106. Communicating with end regions of the receptacle 106 are the closure member mounted inlet and outlet gas conduits 120 and 122 which convey a gas stream under measurement into and away from the receptacle 106. Representative overall dimensions for the housing member 102 are shown at 114, 116 and 118 in FIG. 1, and a thickness dimensions for the closure member 104 is indicated at 128 in FIG. 1.

As is described below herein, it is desirable to maintain control over the operating temperature of a detection cell received in the receptacle 106 during use of the FIG. 1 apparatus. The presence of a combined heating/refrigeration apparatus in the FIG. 1 detection apparatus is indicated at 124 with a heat energy communicating path indicated at 126 in FIG. 1. The combination of an electrical resistance element with a Peltier effect semiconductor junction device may be used to embody the heating/refrigeration apparatus shown at 124 at FIG. 1, or alternatively, a gaseous refrigeration machine or other heating and cooling arrangements known in the art may be employed.

FIG. 2 in the drawings shows a detection cell made in accordance with the invention which may be used in the FIG. 1 detector apparatus for sensing the presence of chlorine or other gaseous halogen molecules in a flowing stream of gases. The detection cell 200 in FIG. 2 is shown in exploded perspective and consists of a thin film electrical resistance element 204 which is mounted in a substrate member 202 and then received on a carrier member 206 for housing in the receptacle 106 of FIG. 1 or in some other containment apparatus. Typical dimensions for a detection cell of the FIG. 2 type are shown at 230, 232, 234 and 236 in FIG. 2, the first three of these dimensions representing the length, width, and thickness of the substrate member 202 and the latter dimension representing the thickness of the thin film electrical resistance element 204.

The response of the FIG. 2 detection cell to the incidence of halogen gase is measured by way of changes in the electrical resistance of the thin film resistance element 204; such resistance change is sensed by way of the four-lead or four-point electrical measurement circuit generally indicated at 211 in FIG. 2. The electrical measurement circuit 211 consists of a current source 224 which is applied to outward extremity portions of the thin film resistance element 204 and a voltage measuring apparatus 222 which is used to measure the voltage drop induced across a selected portion of the resistance element 204 by the current from the source 224.

Current from the source 224 is applied to convenient prepared extremity points on the thin film structure 204 such as the equipotential face indicated at 212 in FIG. 2 and a similar face on the opposite end of the thin film element 204. Current application is by way of the electrical leads 218 and 220 which attach to the equipotential faces by way of thermal compression bonding, welding, or other attachment arrangements known in the thin film art. The equipotential faces 212 may reside on the top surface of the thin film resistance element in lieu of being located on the ends, as is represented in FIG. 2.

Voltage drop across the major portion of the resistance element 204 is sampled by way of the voltage measuring apparatus 222 and its leads 214 and 216 which attach to suitably prepared pad areas 210 and 228 that are disposed inward from the equipotential faces 212 but nevertheless toward extremities of the resistance element 204. Separation of the current and voltage nodes in the four-lead electrical measurement circuit 211 is, of course, desirable in order that the voltage signal observed at 222 represents only the voltage occurring across the body of the thin film resistance element 204 and exclude voltage components originating in the attachments between leads 218 and 220 and the equipotential surfaces and the body of resistance element 204.

The flows of the unknown or gas being tested by the FIG. 2 detection cell are indicated at 226 and 227 inig. 2. These dual flows are provided in keeping with one aspect of the invention wherein chemical and/or physical reactions between the gas components being detected and elements of the FIG. 2 detection cell occur not only on the gas exposed surfaces of the electrical resistance element 204, but also on the surfaces of the substrate member 202. Provision for the flow 226 and the reaction of unknown gas with the underlying major surface of the substrate 202 is provided by the separation flow space indicated at 208 in FIG. 2 and by the illustrated greater width of the carrier member 206 with respect to the substrate member 202. Other arrangements of the thin film electrical resistance element, substrate member 202 and carrier member 206 which provide for unknown gas flow over the resistance element and substrate surfaces are, of course, possible within the purview of the invention.

According to one aspect of the present invention, halogen components in the flow of unknown gases indicated at 227 in FIG. 2 reacts physically and chemically with the exposed surfaces of the thin film electrical resistance element 204 to release heat energy; this heat energy in turn elevates the temperature of the resistance element 204 and thereby changes its electrical resistance and the voltage measured at 222. The physical portion of the gas to thin film electrical resistance element reaction may involve either one or both of the phenomena of adsorption and absorption. Parenthetically, it is notable that in thin film settings, the distinction between the phenomena of adsorption and absorption is recognized to become somewhat academic in nature. These two phenomena are therefore referred to with the generic name "sorption" herein.

In addition to this sorption phenomenon between unknown gas and thin film resistance element 204, the detection cell 200 also employs the phenomenon of sorption between halogen components of the unknown flow and the substrate member 202. This additional reaction is also a heat energy liberating phenomenon with the liberated heat energy being conveyed by way of the intimate relationship between the substrate 202 and the resistance element 204 into the resistance element 204 where additional quantums of electrical resistance change result.

In addition to this communication of heat energy between the substrate 202 and the thin film resistance element 204, and in accordance with another aspect of the invention, the reaction of halogen components with the metal of the thin film electrical resistance element 204 and the metal halide of the substrate member 202 promote an enhanced diffusion of the halide salt ions produced at the surfaces of the electrical resistance element 204 into the crystalline structure of the metal halide substrate member 202. Conversely, the chemical halogen reaction produced in the crystalline metal halide substrate member 202 will experience enhanced diffusion into the thin metallic film of the electrical resistance element 204. This latter diffusion of substrate generated ions into the electrical resistance element 204 contributes yet another component to the electrical resistance change measured by the voltage at 222—a change responding to the incidence of halogen ions into the detection cell 200. In this later diffusion process, the change of the metallic thin film element's electrical resistance will be proportional to the concentration of the diffused, ionically-bonded impurities which act as electron scattering centers in the electrical resistance element 204. This change of electrical resistance will, in turn, be proportional to the concentration of the halogen gas that is initially sorbed.

These sorption reactions are supplemented by conventional chemical reactions which occur at the surfaces of the electrical resistance element 204 and the substrate member 202, the latter reaction being sensed by way of the thermal coupling between substrate and the thin film resistance element.

In order to achieve these several reactions between halogen components in the unknown gas stream and the thin film resistance element and the substrate member, a selection of materials used in fabricating the thin film resistance element and in the substrate member is necessary. One possible selection of materials for the FIG. 2 detection cell consists of the combination of a thin film resistance element 204 that is composed of metallic silver and a substrate member 202 which is composed of crystalline cesium bromide. If the silver-cesium bromide arrangement of the FIG. 2 detector is exposed to chlorine gas in a contaminated atmosphere, the chlorine gas will be sorbed on the metallic thin film and the following chemical and thermodynamic reactions will occur.

In the thin film element, the reaction:

$$Cl_2 + 2Ag \rightarrow 2AgCl + Q \tag{1}$$

while in the metal halide substrate member 022, the reaction:

$$AgCl + CsBr \rightarrow AgBr + CsCl + Q \tag{2}$$

are to be expected.

The reactions of these two equations proceed in the indicated left to right direction and liberate heat energy in accordance with the Gibbs free energy phenomenon which is known in the art and which is explained, for example, in the published work entitled "Physical Chemistry", which is written by Clyde R. Metz and published by the McGraw-Hill Book Company, New York, 1976.

Table I shown below lists 21 possible metal and metal halide pair combinations, including the above silver and cesium bromide combination which might be employed in fabricating the FIG. 2 detection cell 200. The combinations of Table 1 are formulated according to the conditions implicit in the general reaction reaction:

$$nM_1Cl_m + mM_2\Gamma_n \rightarrow mM_2Cl_n + nM_1\Gamma_m + Q \tag{3}$$

where
- $M_1$ is the thin, conducting metallic surface film material;
- $M_2$ is the metal selected for the metal halide substrate member ($M_1 \neq M_2$);
- $\Gamma$ is the halogen selected for the metal halide substrate member;
- m and n are stoichiometric coefficients; and
- Q is the heat energy liberated as a result of the reaction.

The Table I set of combinations was formulated according to the conditions implicit in equation 3; that is, a reaction between the thin film of the resistance element 204 and the incident halogen gas must be possible. If the theoretical change in isobaric and isothermic potentials, that is, the change in the Gibbs free energy level for each thin metallic film resistance element in Table I is identified as shown in the second column of Table I, the values of $\Delta G$, that is the change of the Gibbs free energy, may be interpreted as follows:

A negative value of $\Delta G$ indicates the detection of chlorine is possible.

A positive value of $\Delta G$ indicates the impossibility of detecting chlorine gas.

TABLE I

| Metal/Metal Halide Combination | Change of the Isobar-Isotherm Potential ($\Delta G$) [kcal/mole] |
|---|---|
| Ag/CsBr | −2.8 |
| Ag/KBr | −3.3 |
| Ag/KI | −9.6 |
| Ag/LiF | +29.8 |
| Al/CsI | +22.0 |
| Al/KBr | +13.5 |
| Al/KI | +16.0 |
| Bi/CsI | −21.1 |
| Bi/KI | −28.0 |
| Cu/CsBr | −4.3 |
| Cu/KI | −12.0 |
| Cu/LiI | −27.0 |
| Cu/NaBr | −10.0 |
| Cu/NaI | −19.4 |

TABLE I-continued

| Metal/Metal Halide Combination | Change of the Isobar-Isotherm Potential ($\Delta G$) [kcal/mole] |
|---|---|
| In/CsBr | +2.0 |
| In/KI | +5.0 |
| Mn/KBr | +2.9 |
| Mn/KL | +6.0 |
| Pb/CsI | −1.8 |
| Pb/KI | −7.0 |
| Tl/KBr | −6.4 |

In the Table I listing therefore, 13 of the identified metal and metal halide pairings, that is, the pairings having a negative number in the right-hand column of Table I, are potentially useful in the FIG. 2 detection cell apparatus. It is, of course, possible that some of the halide substrate compounds recited in the the left-hand column in Table I are impractical for use in the FIG. 2 apparatus according to the present state of the metal halide art. These compounds are nevertheless possessed of the desired energy relationship characteristics with respect to at least the halogen, chlorine, for use in the FIG. 2 apparatus and are, therefore, recited inTable I. Physical strength properties or other characteristics of some Table I listed compounds may also require modification of the support structure or other of the arrangements shown in the FIG. 2 apparatus.

It is notable that a detection cell made in accordance with the presently described concepts has the characteristics of cumulative non-recovering indication of reactant gas exposure. As is described in connection with the blocks 300 and 302 in FIG. 3 below, this cumulative exposure response is useful in some applications of the invention such as dosimeter devices, but also necessitates the consideration of exposure time interval and the negation or nulling out of previous exposure history in the case of a concentration measuring instrument made according to the invention.

The metal halide composition of the substrate member 202 provides an affinity for halogen gas components in the unknown gas flows 226 and 227 across the FIG. 2 detection cell surfaces. By considered selection of the thin film metal and metal halide pairings from Table I moreover, the degree of this affinity for a particular halogen can be emphasized in a particular use of the invention. In addition to such a "first level" enhancement of selectivity in a FIG. 2 detection cell to a particular halogen gas, it is also possible to increase the selectivity of an apparatus using the FIG. 2 detection cell, and thereby reduce or eliminate the possibility of spurious response to some component other than the intended halogen gas, by using a plurality of the FIG. 2 detection cells as component cells in a detector array.

Since each of the metal and metal halide pairings in Table I has a unique Gibbs free energy or $\Delta G$ value in the right-hand column of Table I, an array of multiple detection cells, each of a different Table I pairing and mounted in a common holder of the FIG. 1 type, will generate a plurality of electrical resistance responses that is unique in accordance with the type of gas in the unknown stream. According to this concept, if several discrete detector elements are fabricated from the universe of possible combinations shown in Table I and mounted in a common chamber of the type shown in FIG. 1, the incidence of a low concentration of chlorine gas, for example, will produce a distinct electrical resistance change in each detector element, and the array of these resistance change values is unique to chlorine gas since any other gas will produce a different ratio of resistance changes inthe array than will a change of chlorine concentration or the introduction of elements in addition to chlorine to the unknown stream. By way of this array of multiple resistance change signals, it is also possible to select response patterns that are identifiable for each of the different halogen gases of interest in a detection environment.

Electrical signal multplexing as is commonly practiced with microprocessors and other computer devices, may be employed for the collection of multiple signals from a detector array. Processing of the electrical resistance change signals for each detection cell in the array is based on the absolute resistance change displayed by each cell and also on the ratio and difference comparisons of the change in individual cell resistances.

Figure 3:
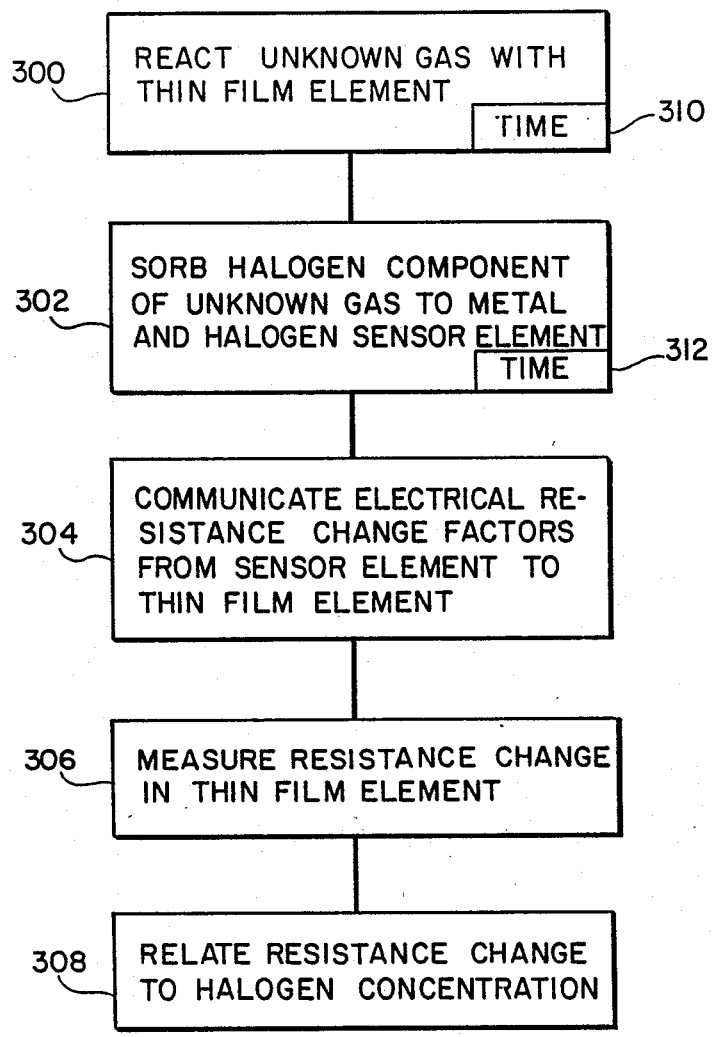
FIG. 3 shows an operating sequence for a detection cell in accordance with the invention.

FIG. 3 in the drawings illustrates the method of the present invention halogen detection. In the FIG. 3 steps, the reaction of an unknown gas with the thin film electrical resistance element 104 is indicated in the block 300 while the reaction of the unkniown gas halogen component with the selective metal halide substrate is indicatd in the block 302 and the communication of liberated energy and the ionic communication between substrate and thin film resistance element is indicated in the block 304. Measurement of the electrical resistance change in the thin film element, as is performed by the electrical measurement circuit 211 in FIG. 2, is indicated in the block 306 of FIG. 3 and the correlation of resistance change to halogen gas concentration is indicated in the block 308.

Since the physical/chemical reaction between halogen gas and halide substrate and metallic thin film elements is unidirectional or irreversible in nature—insofar as the present instrumentation environment is concerned, the electrical resistance changes experienced in the thin film element 204 include a cumulative or past history related component which is both desirable and also in some uses of the apparatus, necessitating of additional apparatus complexity in order to be accommodated.

In a dosimeter application of the FIG. 2 detection cells, this cumulative effect has the desirable ability of measuring the integrated or "area under the curve" total exposure of the dosimeter's test subject when read out following an extended period of exposure or exposure and non-exposure intervals. The cumulative exposure nature of the FIG. 2 cell characteristics is therefore a desirable characteristic in dosimeter uses of the invention.

In an instrument which measures concentration of a component gas in an unknown flow, the cumulative nature of the detector element resistance change must be taken into consideration and the "non-zero" starting point for a new exposure recognized. Electrical bridge circuitry and other known differential measurement techniques in which comparison with a non-zero reference or initial value of an unknown, in fact, compensates for the non-zero value of the initially measured signal. These techniques can also be used to accommodate this cumulative effect non-zero starting point in a sensor.

The duration of the exposure time between halogen gas and sensing elements is also a consideration in an integrating or cumulative effect sensor, since it allows segregation of a resistance change arising from long exposure to a low concentration and the same resistance change arising from a short duration exposure to a high concentration of the same gas. Consideration of exposure time, as indicated symbolically at 310 and 312 in the FIG. 3 method sequence, can be embodied in the FIG. 2 apparatus in the form of time-gated control of the flows 226 and 227.

While the apparatus and method herein described constitute a preferred embodiment of the invention, it is to be understood that the invention is not limited to this precise form of apparatus or method, and that changes may be made therein without departing from the scope of the invention, which is defined in the appended claims.

I claim:

1. Apparatus for detecting the presence of gaseous first halogen components in an unknown mixture of gases comprising the combination of:
   a detection substrate member comprised of a second halogen chemical compound of a first metal;
   a thin film electrical resistance detector element received on said substrate member and comprised of a second metal in thin film metallic form;
   means for moving a stream of said unknown gas mixture over said detection substrate and detector elements; and
   means responsive to the combined detector element unknown gas exposure and the substrate member unknown gas exposure resistance changes in said detector element for indicating the presence of said first halogen components in said unknown mixture of gases.

2. The apparatus of claim 1 wherein said means for indicating the presence of the first halogen components includes a four-point electrical resistance measurement apparatus connected with said thin film electrical resistance detector element.

3. The apparatus of claim 1 wherein said first halogen components include chlorine.

4. The apparatus of claim 1 wherein said second halogen compound of a first metal and said second metal are each materials having a negative Gibbs free energy change chemical reaction with said first halogen components.

5. The apparatus of claim 4 wherein said thin film second metal and said subtrate member halogen chemical compound are comprised of materials taken from the pair groups consisting of silver with potassium bromide, silver with potassium iodide, bismuth with cesium iodide, bismuth with potassium iodide, copper with cesium bromide, copper with potassium iodide, copper with lithium iodide, copper with sodium bromide, copper with sodium iodide, lead with cesium iodide, lead with potassium iodide, thallium with potassium bromide and silver with cesium bromide.

6. The apparatus of claim 5 further including additional of said detection substrate member and thin film electrical resistance detector element combinations disposed in said gas stream with each of said combinations comprising a different one of said pair groups.

7. The apparatus of claim 6 further including electrical resistance sensing means for determining the halogen gas responsive resistance change in each of said detector element combinations and for comparing the responses of plural of said detector element combinations.

8. The apparatus of claim 1 wherein said thin film electrical resistance detector element has a thickness in the range of four hundred to eight hundred angstroms.

9. The apparatus of claim 1 wherein said thin film electrical resistance element is received on said substrate member during one of the processing arrangements of vacuum thermal evaporation, electron beam evaporation, and direct current sputtering.

10. The apparatus of claim 1 wherein said means for moving a stream of said unknown gas mixture includes temperature and gas flow rate control means for maintaining controlled measurement conditions.

11. The method of sensing first halogen element components in a gaseous mixture comprising the steps of:
    conducting a stream of said gaseous mixture over an exposed surface of a thin film first metal detector element;
    conveying a stream of said gaseous mixture over an exposed surface of the detector element supporting substrate member, said substrate member being comprised of a second metal chemically compounded with a second halogen element and being intimately mated physically with said thin film element;
    measuring the electrical resistance change produced in said detector element by the combined reaction of said first halogen element components with said detector element metal and with said substrate member compound; and
    correlating said electrical resistance change with a predetermined resistance to halogen element concentration relationship.

12. The method of claim 11 wherein said conducting and conveying steps comprise disposing a substrate supported detector element in a single gaseous mixture stream.

13. The method of claim 12 wherein said detector element metal and said substrate member halogen compound are taken from the pair groups consisting of silver with potassium bromide, silver with potassium iodide, bismuth with cesium iodide, bismuth with potassium iodide, copper with cesium bromide, copper with potassium iodide, copper with lithium iodide, copper with sodium bromide, copper with sodium iodide, lead with cesium iodide, lead with potassium iodide, thallium with potassium bromide and silver with cesium bromide.

14. The method of claim 13 further including disposing a plurality of substrate supported detector elements each consisting of a different one of said pair groups in said gaseous mixture stream.

15. A method for measuring first halogen element concentrations in a gaseous effluent mixture comprising the steps of:
    reacting said gaseous mixture with a thermally responding metallic thin film electrical resistance element;
    sorbing first halogen components of said gaseous mixture with a thermally responding solid state metal plus second halogen element thermal compound sensor element;
    communicating heat energy from said sensor element sorbing steps to said thin film electrical resistance element; and
    correlating said resistance change with a predetermined resistance change to first halogen element concentration relationship.

16. The method of claim 15 further including the step of cross-diffusing first halogen element reaction ions from said sensor element into said thin film electrical resistance element and from said thin film electrical resistance element into said sensor element;

whereby an additional first halogen element chemical reaction generated component of thin film electrical resistance change is added to the measured electrical resistance change.

17. The method of claim 15 further including repeatiang said reacting, sorbing, communicating, measuring and correlating steps for each of additional of said thin film electrical resistance and said second halogen element chemical compound sensor elements.

18. The method of claim 15 wherein said metallic thin film electrical resistance element and said second halogen element chemical compound sensor element are comprised of metals and second halogen chemical compound materials taken from the pair groups consisting of silver with cesium bromide, silver with potassium bromide, silver with potassium iodide, bismuth with cesium iodide, bismuth with potassium iodide, copper with cesium bromide, copper with potassium iodide, copper with lithium iodide, copper with sodium bromide, copper with sodium iodide, lead with cesium iodide, lead with potassium iodide, thallium with potassium bromide and silver with cesium bromide.

* * * * *